US009839517B2

(12) United States Patent
Centola et al.

(10) Patent No.: US 9,839,517 B2
(45) Date of Patent: Dec. 12, 2017

(54) IMPLANTABLE DEVICE FOR TREATING MITRAL VALVE REGURGITATION

(71) Applicant: NVT AG, Muri AG (CH)

(72) Inventors: Marcos Centola, São Paulo (BR); Emilia Kawa, Hechingen (DE)

(73) Assignee: NVT AG, Muri (CH)

( * ) Notice: Subject to any disclaimer, the term of this patent is extended or adjusted under 35 U.S.C. 154(b) by 0 days.

(21) Appl. No.: 14/865,436

(22) Filed: Sep. 25, 2015

(65) Prior Publication Data

US 2016/0089238 A1 Mar. 31, 2016

(30) Foreign Application Priority Data

Sep. 26, 2014 (EP) ..................................... 14186503

(51) Int. Cl.
*A61F 2/24* (2006.01)

(52) U.S. Cl.
CPC .......... *A61F 2/2445* (2013.01); *A61F 2/2418* (2013.01); *A61F 2230/0069* (2013.01); *A61F 2230/0071* (2013.01)

(58) Field of Classification Search
CPC .... A61F 2/2418; A61F 2/2412; A61F 2/2415; A61F 2/2445
See application file for complete search history.

(56) References Cited

U.S. PATENT DOCUMENTS

| 5,332,402 | A | 7/1994 | Teitelbaum |
| 2006/0058871 | A1 | 3/2006 | Zakay et al. |
| 2010/0217382 | A1 | 8/2010 | Chau |
| 2011/0313515 | A1 | 12/2011 | Quadri |
| 2014/0018915 | A1 | 1/2014 | Biadillah |
| 2014/0031928 | A1 | 1/2014 | Murphy |
| 2014/0121763 | A1 | 5/2014 | Duffy et al. |

FOREIGN PATENT DOCUMENTS

| EP | 2 478 868 | 7/2012 |
| JP | 2013533025 A | 8/2013 |
| JP | 2013540467 A | 11/2013 |
| WO | WO 2009/132187 | 10/2009 |
| WO | WO 2013/178335 | 12/2013 |

OTHER PUBLICATIONS

Extended European Search Report for related European Application No. EP 14 186 503.0, dated Mar. 19, 2015, 7 pages.
Japanese Office Action for Application No. 2015188966 dated Aug. 9, 2016, 6 pages.
English Translation of Japanese Office Action for Application No. 2015188966 dated Aug. 9, 2016, 4 pages.

*Primary Examiner* — Jason-Dennis Stewart
(74) *Attorney, Agent, or Firm* — Reising Ethington, P.C.

(57) ABSTRACT

An implantable device for treating mitral valve regurgitation, the device being configured to expand from a compressed state into an expanded state. The device comprises a stent element consisting of (i) an atrial anchoring stent-portion, and (ii) a valve-carrying stent-portion being fixedly connected with one another, and a valve-element. The atrial anchoring stent-portion has a balloon-like shape and the valve-carrying stent-portion has a cylindrical shape, such, that the valve-carrying stent-portion is positioned intra-annular without contacting the annulus of a native mitral valve.

14 Claims, 3 Drawing Sheets

IMPLANTABLE DEVICE FOR TREATING MITRAL VALVE REGURGITATION

CROSS REFERENCES TO RELATED APPLICATIONS

This application is claims priority from European patent application EP 14186503.0, filed on Sep. 26, 2014, the entire content of which is incorporated herein by reference.

FIELD

The present invention concerns an implantable device for treating heart valve regurgitation and the use of such a device for treating a diseased or otherwise dysfunctional heart valve, preferably of the mitral valve.

BACKGROUND

The mammalian heart comprises four chambers, i.e. two atria, which are the filling chambers, and two ventricles, which are the pumping chambers. In a mammalian heart, there are four heart valves present which normally allow blood to flow in only one direction through the heart, whereby a heart valve opens or closes depending on the differential blood pressure on each side.

The four main valves in the heart are the mitral valve, representing a bicuspid valve, and the tricuspid valve, which are between the upper atria and the lower ventricles, respectively, and thus are called atrioventricular (AV) valves. Further, there are the aortic valve and the pulmonary valve which are in the arteries leaving the heart. The mitral valve and the aortic valve are in the left heart and the tricuspid valve and the pulmonary valve are in the right heart.

The valves incorporate leaflets or cusps, wherein each valve has three cusps, except for the mitral valve, which only has two.

The mitral and the tricuspid valve are situated, respectively, between the atria and the ventricles and prevent backflow from the ventricles into the atria during systole. They are anchored to the walls of the ventricles by chordae tendineae which prevent the valves from inverting. The chordae tendineae are attached to papillary muscles that cause tension to better hold the valve. Together, the papillary muscles and the chordae tendineae are known as the subvalvular apparatus. While the function of the subvalvular apparatus is to keep the valves from prolapsing into the atria when they close, the subvalvular apparatus, however, has no effect on the opening and closure of the valves, which is caused entirely by the pressure gradient across the valve.

During diastole, a normally-functioning mitral valve opens as a result of increased pressure from the left atrium as it fills with blood (preloading). As atrial pressure increases above that of the left ventricle, the mitral valve opens. Opening facilitates the passive flow of blood into the left ventricle. Diastole ends with atrial contraction, which ejects the final 20% of blood that is transferred from the left atrium to the left ventricle, and the mitral valve closes at the end of atrial contraction to prevent a reversal of blood flow.

Several different kinds of valve disorders are known, such as stenosis, which occurs when a heart valve doesn't fully open due to stiff or fused leaflets preventing them from opening properly, or prolapse, where the valve flaps do not close smoothly or evenly but collapse backwards into the heart chamber they are supposed to be sealing off.

Valve regurgitation (backward flow) is also common problem, and occurs when a heart valve doesn't close tightly, as a consequence of which the valve does not seal and blood leaks backwards across the valve. This condition—also called valvular insufficiency—reduces the heart's pumping efficiency: When the heart contracts blood is pumped forward in the proper direction but is also forced backwards through the damaged valve. As the leak worsens, the heart has to work harder to make up for the leaky valve and less blood may flow to the rest of the body. Depending on which valve is affected, the condition is called tricuspid regurgitation, pulmonary regurgitation, mitral regurgitation, or aortic regurgitation.

Mitral regurgitation, i.e. the abnormal leaking of blood from the left ventricle through the mitral valve and into the left atrium when the left ventricle contracts, is a common valvular abnormality, being present in 24% of adults with valvular heart disease and in 7% of the population 75 years of age. Surgical intervention is recommended for symptomatic severe mitral regurgitation or asymptomatic severe mitral regurgitation with left ventricular dysfunction or enlargement. Surgical treatment of severe degenerative mitral regurgitation has evolved from mitral valve replacement to mitral valve repair, since a mitral valve repair has proven to produce superior outcomes.

Meanwhile, mitral valve repair and replacement has also been achieved using minimally invasive procedures. The desire for less invasive approaches is linked with the fact that a significant proportion of patients, especially elderly persons or those with significant comorbidities or severe left ventricular dysfunction, are not referred for (open heart) surgery.

Various percutaneous technologies have emerged and are at different stages of development. Current percutaneous technologies for mitral valve repair or replacement are, e.g., percutaneous mitral valve replacement, enhanced mitral coaptation, edge-to-edge-percutaneous mitral valve repair (plication), percutaneous chordal repair, percutaneous mitral annuloplasty, and left ventricle remolding.

However, the different percutaneous repair approaches do still not offer the same degree of efficacy as a surgical repair of the mitral valve.

While the technology of percutaneous mitral valve replacement is a possible alternative in a selected group of patients with a low probability of successful repair, the challenges of this technique are very high: the mitral annulus has an asymmetrical saddle shape, and different anchoring designs might be required for different mitral regurgitation etiologies. Further, left ventricular outflow obstruction might occur due to retained native valve tissue and paravalvular leaks might also pose problems.

E.g., WO 2013/178335 A1 discloses an implantable device for improving or rectifying a heart valve insufficiency, such as mitral valve regurgitation, and comprises a contact strip attached to a closure element, which contact strip forms a loop in the atrium thus contacting the inner wall of the heart and attaching the device therein.

Further US 2014/0121763 A1 discloses a mitral valve prosthesis including a self-expandable frame and two or more engagement arms. The self-expandable frame carries a valve. Each of the engagement arms corresponds to a native mitral valve leaflet. The prosthesis also comprises anchor attachment points, by means of which anchors are attached for anchoring the prostheses in the heart.

SUMMARY

In view of the above, there still is the need for a heart valve prosthesis by means of which heart valve regurgitation can be efficiently treated, while at the same time traumatic impact on the heart is minimized.

Described herein is an implantable device for treating heart valve regurgitation, the device being configured to expand from a compressed state into an expanded state, and comprising: —a stent element consisting of (i) an atrial anchoring stent-portion, and (ii) a valve-carrying stent-portion, the atrial anchoring stent-portion being fixedly connected with the valve-carrying stent-portion; the atrial anchoring portion, in the expanded state of the device, has a balloon-shape/balloon-like shape and has a diameter (d1) which is larger than the diameter of an annulus of a native heart valve present between an atrium and a ventricle of a heart to be treated, and is sized and configured to anchor the device via radial force in an atrium of a heart to be treated when the device is in the expanded state; further, the valve-carrying stent-portion, in the expanded state of the device, has a substantially cylindrical shape with a preferably continuous diameter d3 along its cylindrical length (l), which diameter d3, in the expanded state, is smaller than the diameter of the annulus of the native heart valve, such that there is no contact between the annulus of the native heart valve and the valve-carrying stent-portion, and enabling the native heart valve to retain its function. The implantable device also comprises a valve element comprising a skirt-portion and a valve-portion, with the skirt-portion being externally mounted to the valve-carrying stent-portion, and with the valve-portion being internally mounted to the valve-carrying stent-portion.

With the implantable device and its use in the treatment of heart valve regurgitation, in particular of mitral valve regurgitation, it is possible to securely and conveniently position the implantable device in the heart of a patient to be treated: via its anchoring stent-portion the implantable device is anchored in the atrium of a patient's heart, preferably in the left atrium of a heart, while its valve-carrying stent-portion is retained intra-annular; thereby, the native annular structure is not touched by the device, and the— dysfunctional—native valve, as far as it can open and close, can still function, as far as its condition allows. This is possible due to the fact that the implantable device has a valve-carrying portion with a diameter which is smaller than the diameter of the native valve.

The atrial anchoring stent-portion, thus, represents a self-expandable anchor element with a balloon- or ball-shaped form, which is placed inside the left atrium space and fixed in the atrium by radial force. As the internal atrial main cavity has an almost spherical anatomy this element, using a ball-in-ball radial compression arrangement, retains the necessary stability to keep the implanted valve, or rather the valve-carrying stent-portion, inside the intra-annular space without touching the annular structure.

With this arrangement, the native valve, which does not close completely, is not replaced: rather, the native valve's leaflets—as does the valve of the implantable device—opens in diastolic phase, allowing the blood to enter the left ventricle without restriction. In systolic phase, i.e. when the left ventricle contracts, the valve of the implantable device, as well as the native valve still can, close, wherein the valve of the implantable device serves as a spacer, enhancing the coaptation of the native mitral leaflets. In other words, the native valve's leaflets, during systolic phase, close/abut against the valve-carrying portion of the implantable device, while the valve of the implantable device closes intra-annular, thus guaranteeing proper closure between the atrium and the left ventricle during systole.

Thus, with the device, an effective hybrid solution for treating heart valve regurgitation is provided, comprising means for mitral replacement combined with means for an enhanced coaptation.

Presently, the term "balloon-like" is meant to comprise any bulbous, or rounded shape, which also can, but does not have necessarily, taper at one end; accordingly, the "balloon-like" shape also comprises spherical or ball-like forms.

Presently, and as generally understood, the term "stent" is meant to comprise a cylindrical, tubular, or otherwise shaped radially-expandable metal frame or body, and, thus, comprises any device or structure that adds rigidity, expansion force, or support to a prosthesis, while "stent graft" refers to a prosthesis comprising a stent and a graft material associated therewith that forms a fluid-tight or substantially fluid-tight lumen through at least a portion of its length. The body of stents/stent grafts is inserted into the vessel/organ to be treated and is expanded or self-expandable and fixed or fixes itself at the appropriate site in order to keep open the lumen of the vessel/organ or in order to anchor a prosthesis comprising the stent.

The metal frame of the stent members and elements of the device can be laser cut or woven or braided or knitted or comprise an otherwise interconnected metal mesh.

Stent and/or stent grafts generally comprise, for example, a series of stent elements or, respectively, a wire framework made of a self-expanding material.

In this regard it is noted that the anchoring stent-portion is designed such, that it is not covered or at least partially not covered in order to allow the pulmonary veins to deliver the blood from the lungs into the left atrium; thus, it is necessary that the blood flow into the left atrium is not obstructed by the atrial stent-portion.

The valve-carrying stent-portion may also represent single metal rings forming a metal mesh, the rings meandering circumferentially and being disposed successively in the valve-carrying stent-portion's longitudinal axis/direction, wherein the metal rings have a Z-shaped profile with pointed arches pointing alternately toward the proximal end and distal end of the device. The metal rings are, thus, indirectly connected via the skirt-portion of the valve.

Presently, the expressions "substantially cylindrical" or "a substantially cylindrical shape" or a "substantially cylindrical form" presently mean any three-dimensional form that has a certain length, and that has a substantially round cross section, wherein also forms are comprised the cross sections of which are, e.g., an ellipse, parabola, or hyperbola, and wherein the cross-section does not necessarily need to have a regular circumference, but also includes irregular circumferences, as long as the substantially cylindrical form of the valve carrying stent-portion is retained. Also, with the expression "substantially cylindrical" forms are comprised which conform or substantially conform to the treated valve anatomic annulus shape.

Similar, the expression "substantially continuous" in connection with the diameter of the substantially cylindrical shape of the valve-carrying stent-portion means that, generally, the diameter of the cylindrical form is about the same over its length, wherein it will be clear to one skilled in the art that there can be minor or slight variations in diameter due to manufacturing issues.

The components of the device, e.g., the stent-element comprising the anchoring stent-portion and the valve-carrying stent-portion including the valve, can be variously sized (e.g., length, diameter, etc.) as suitable for an intended use and as depending on the respective condition and shape and dimension of the patient's heart, wherein the anchoring stent-portion's diameter, in the expanded state, is preferably larger than the atrium's diameter in order to allow a secure fixation of the implantable device in the atrium.

According to a preferred embodiment, the stent element of the implantable device is self-expanding, wherein the device is configured, such, that it is convertible from a compressed state for introducing the device into a heart of a mammal to an expanded state within the heart.

According to a preferred embodiment, the valve-element, upon implantation of the device, is sized and configured such, that the native heart valve's function is supported without replacing or impairing the native heart valve's function.

With the "native heart valve's function", presently, the opening and closing of the heart valve, preferably the mitral valve, is meant, as far as the heart valve is closing. The latter means that if the native heart valve's function's is impaired as such, i.e. prior to the implantation of the implantable device according to the invention, it does not properly close leading to a leaking a heart valve regurgitation. However, upon implantation of the device, the leaflets of the diseased heart valve can still perform a closing movement, while it is obvious that they will abut against the valve-carrying stent-portion of the implantable device.

According to another embodiment of the implantable device, the atrial anchoring stent-portion and the valve-carrying stent-portion are integrally formed.

According to this embodiment, the atrial anchoring stent-portion and the valve-carrying stent-portion are manufactured in one piece. This embodiment is advantage over devices comprising a stent-element that has been fabricated from two different stent-portions due to facilitated manufacturing processes. Whilst the one-piece-stent-element is preferred, embodiments comprising a two- or more-piece stent-element, joined or coupled together, can also be realized and are comprised within the meaning of the present disclosure.

According to another embodiment of the device, the atrial anchoring stent-portion is anchorable in the atrium of a heart, such, that the anchoring stent-portion at least partially contacts the atrium walls.

As mentioned above, the expandable atrial anchoring stent-portion expands, in the expanded state of the device, within the atrium of the heart of a patient to be treated, and, thus, anchors or fixates the whole device within the heart. Due to the dimensions of the atrial anchoring device, the anchoring stent-portion, upon expanding, anchors itself and at least partially abuts to the atrial walls thereby also anchoring the other portions of the device. As a consequence, the valve-carrying stent-portion of the stent-element is positioned and fixated intra-annular without touching the native annular structures.

According to another preferred embodiment, in the device, the skirt-portion and the valve-portion of the valve element are made of the same material, preferably pericardium from a mammal.

Accordingly, in a preferred embodiment, the biological valve and the skirt comprises or consists of a material that is selected from animal pericardium, in particular porcine, bovine, equine pericardium, or from native leaflets from human heart or veins.

In yet another preferred embodiment of the valve according to the invention, the valve-element comprises a bi- or tri-leaflet valve.

The healthy human tricuspid valve comprises three leaflets, or cusps, named after their positions: anterior, posterior and septal. Thus, according to one aspect, the valve of the stented valve mounted on the stent graft member also comprises three leaflets, and thus, represents a tricuspid valve, whilst also a valve having only two leaflets and, having, thus, a "bicuspid" architecture, or with even one leaflet, i.e. a monocuspid valve, can be used with the implantable device.

The human mitral valve has two leaflets, the anterior leaflet which has a semi-circular shape, and the posterior leaflet which has a quadrangular shape.

As mentioned above, such valves can be created from human or animal donors. They can be created, e.g., from pericardium of human or any mammal, or from native leaflets from the heart or veins, or from any other biological material suitable for the intended purpose. Generally speaking, such valves are also called biological or tissue valves—as contrary to mechanical valves.

According to another embodiment, in the device according to the invention the stent-element is made of a shape-memory material, preferably Ninitol. Nitinol has been proven as suitable for implantable medical devices and used in different medical appliances.

In a preferred embodiment of the device, the stent-element is a laser-cut stent-element and/or composed of wires, preferably from Nitinol.

In this regard, it is preferred that the atrial anchoring stent-portion and/or the valve-carrying stent-portion is made from braided or otherwise intersected wires, preferably from Nitinol.

According to yet another embodiment, the atrial anchoring stent-portion and/or the valve-carrying stent-portion is made from wire-loops.

In this embodiment, the anchoring stent-portion has a basket-like form, shaped through the wire loops; in this regard it is preferred that between 3 and 15, preferably at least three, four five six, seven, eight, nine, ten, eleven loops are present.

According to another aspect of the device, the device further comprises visualization elements, in particular radio-opaque markers, wherein the visualization elements are attached to the stent-element of the device at one or more positions.

Presently, "visualization elements" shall mean any suitable aid attached or otherwise provided on the device facilitating the accurate placement of the device. According to one aspect, those visualization elements are radiopaque markers comprising or consisting of any suitable material, such as, e.g., gold, tantalum, platinum.

According to another aspect, in the device, the substantially cylindrical shape of the valve-carrying stent-portion, in the expanded state of the device, has a substantially continuous diameter (d3) along its cylindrical length (l).

The present disclosure also relates to a device for use in the treatment of heart valve regurgitation, the heart valve regurgitation being selected from mitral valve regurgitation and/or tricuspid valve regurgitation. In other words, the disclosure also relates to the use of the device for treating heart valve regurgitation, and to a method for treating heart valve regurgitation, the method comprising the step of implanting the implantable device according to the invention and as detailed above.

When delivered by catheter, the method can also include the step of inserting a delivery catheter including the implantable device, the implantable device being in a compressed state when loaded on the delivery catheter loading and upon inserting the device into the heart of a subject that requires the treatment, i.e. is suffering from heart valve regurgitation.

The patient or subject in need of treating, e.g., the patient or subject suffering from heart valve regurgitation, is a mammal, preferably a human.

As mentioned at the outset, heart valve regurgitation is a medical condition of the heart in which a heart valve does not close properly when the heart pumps out blood. Accordingly, mitral regurgitation is the abnormal leaking of blood from the left ventricle through the mitral valve into the left atrium, when the left ventricle contracts. The symptoms for this heart disorder depend on the phase of the disease process the individual is in. Individuals with acute mitral regurgitation will have the signs and symptoms of decompensated congestive heart failure, e.g., shortness of breath, pulmonary edema, orthopnea, and paroxysmal nocturnal dyspnea, as well as symptoms suggestive of a low cardiac output state, e.g., decreased exercise tolerance.

The disclosure also relates to the use of the device for treating tricuspid regurgitation in a mammal, as well as to a method for treating tricuspid regurgitation in a mammal, comprising the step of delivering and/or implanting a device according to the invention to a position within the heart of a patient in need thereof in order to replace or support the native tricuspid valve of said patient.

The device can be either surgically implanted or delivered by transcatheter methods. In the latter case, i.e. with a transcatheter method, the device is loaded onto a suitable deployment catheter, there being compressed by a retractable sheath or tube or similar. The deployment catheter is inserted into the heart of a patient whose tricuspid or mitral valve needs replacement or support.

When the tricuspid valve is to be treated, the deployment catheter having the device loaded thereon in a compressed state, is advanced via the jugular vein into the vena cava superior into the right atrium, where it is deployed in order to expand the anchoring stent-portion in the atrium and the valve-carrying stent-portion intra annular. Alternatively, the deployment catheter having the device loaded thereon in a compressed state can be advanced via the femoral vein into the vena cava inferior into the right atrium. Correct placement can be monitored, e.g., via visualization elements present in the implantable device according to the invention.

Upon correct placement, the sheath or the otherwise compressing means is retracted to stepwise release the device, upon which action the stent members of the device can expand and fixate the device in the vena cava superior and inferior, respectively.

When treating the mitral valve, the deployment catheter having the device loaded thereon in a compressed state, is advanced trans-apical into the left ventricle crossing the mitral valve to the left atrium where it is deployed in order to expand the anchoring stent portion in the atrium and the valve-carrying stent-portion in the intra-annular position. Also, the compressed device can be introduced via the femoral vein or Jugular vein into the right atrium and trans-septal to the left atrium where it is deployed in order to expand the anchoring stent portion in the atrium and the valve-carrying stent-portion in the intra-annular position. Additionally, the compressed device can be introduced via small surgical thoracotomy into to the pulmonic vein (right left inferior superior pulmonic vein) to the left atrium where it is deployed in order to expand the anchoring stent portion in the atrium and the valve-carrying stent-portion in the intra-annular position.

Further advantages and features are set forth in the following description and in the attached figures.

It will be understood that the aforementioned features and the features still to be explained below can be used not only in the respectively specified combination but also in other combinations or on their own, without departing from the scope of the present invention.

BRIEF DESCRIPTION OF THE DRAWINGS

The aforementioned features and the features still to be explained below are shown in the figures, in which.

DESCRIPTION OF PREFERRED EMBODIMENTS

Figure 1:
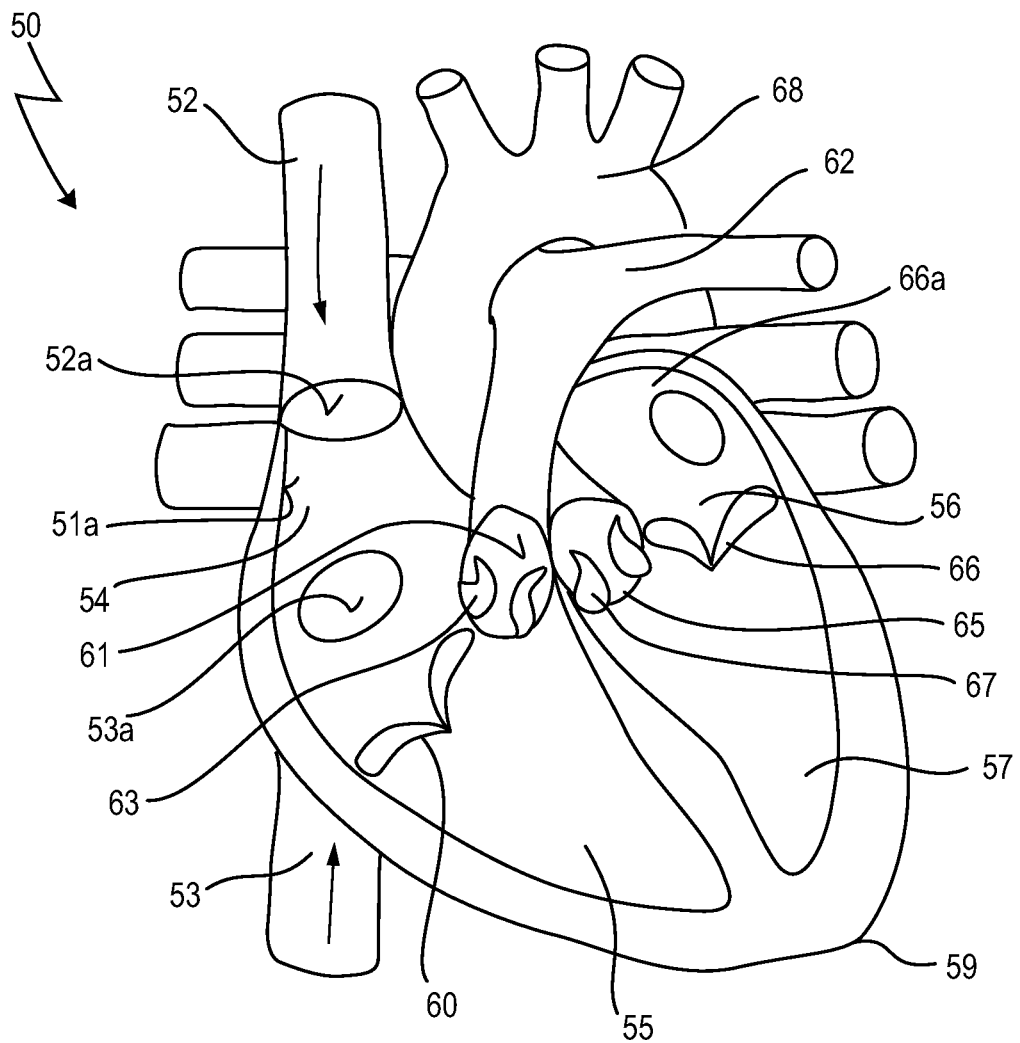
FIG. 1 shows a schematic drawing of a human heart.

In FIG. 1, a human heart 50 is depicted, having a right atrium 54, a right ventricle 55, a left atrium 56 and a left ventricle 57. Also depicted in FIG. 1 is a portion of the vena cava superior 52, entering the heart 50 via the right atrium 54, and a portion of the vena cava inferior 53.

In more detail, the superior vena cava 52 returns the blood from the upper half of the body, and opens into the upper and back part of the right atrium 54, the direction of its orifice 52a being downward and forward. Its orifice 52a has no valve.

The inferior vena cava 53, which has a larger diameter than the superior vena cava 52, returns the blood from the lower half of the body, and opens into the lowest part of the right atrium 54, its orifice 53a being directed upward and backward, and guarded by a rudimentary valve, the valve of the inferior vena cava (Eustachian valve, not shown).

The right ventricle 55 has a triangular in form, and extends from the right atrium 54 to near the apex 59 of the heart 50.

The right atrioventricular orifice (not depicted in FIG. 1) is the large oval aperture of communication between the right atrium 54 and ventricle 55, and is guarded by the tricuspid valve 60.

The opening 61 of the pulmonary artery 62 is circular in form, and is placed above and to the left of the atrioventricular opening; it is guarded by the pulmonary valves 63.

The tricuspid valve 60 consists of three about triangular cusps or segments or leaflets 64, the anterior, posterior and medial or septal cusp. Their bases are attached to a fibrous ring (not depicted in FIG. 1) surrounding the atrioventricular orifice and are also joined to each other so as to form a continuous annular membrane. Their atrial surfaces are directed toward the blood current from the atrium 54, while their ventricular surfaces are directed toward the wall of the ventricle 55; together with the apices and margins of the cusps, they give attachment for the chordae tendineae (not depicted in FIG. 1).

As discussed above, the function of the tricuspid valve is to prevent back flow of blood into the right atrium 54; arrows 70 and 71 indicate normal blood flow into the right atrium 54.

The left atrium 56 is smaller than the right atrium 54. The left ventricle 57 is longer and more conical in shape than the right ventricle 55. The left atrioventricular opening (mitral orifice, not depicted in FIG. 1) is placed to the left of the aortic orifice 65, and is guarded by the bicuspid or mitral valve 66.

The aortic opening 65 is a circular aperture, in front and to the right of the atrioventricular opening, and its orifice is guarded by the three aortic valves 67. Reference number 68 designates the aorta.

Separating the left atrial chamber or left atrium 56 from the left ventricle 57, the mitral valve 66 is, as mentioned above, an atrio-ventricular valve, with the mitral annulus 70 constituting the anatomical junction between the ventricle 57 and the left atrium 56; the annulus 70 also serves as insertion site for the leaflet tissue (not shown).

The normal mitral valve 66 opens when the left ventricle 57 relaxes (diastole) allowing blood from the left atrium 56 to fill the decompressed left ventricle 57. During systole, i.e. when the left ventricle 57 contracts, the increase in pressure within the ventricle 57 causes the mitral valve 66 to close, preventing blood from leaking into the left atrium 56 and assuring that all of the blood leaving the left ventricle is ejected though the aortic valve 67 into the aorta 68 and to the body. Proper function of the mitral valve is dependent on a complex interplay between the annulus 70, leaflets and subvalvular apparatus (not depicted in FIG. 1, respectively).

The mitral valve 66 has two leaflets (not shown), i.e. the anterior and the posterior leaflet. As mentioned above, the anterior leaflet has a semi-circular shape, and the posterior leaflet has a quadrangular shape. The motion of the anterior leaflet defines an important boundary between the inflow and outflow tracts of the left ventricle 57. The anterior leaflet is attached to two fifths of the annular circumference, while the posterior leaflet is attached to approximately three fifths of the annular circumference. The posterior leaflet ahs typically two well defined indentations which divide the leaflet into three individual scallops, which are designated as P1, P2, P3; the three corresponding segments of the anterior leaflet are designated with A1, A2, A3. The Indentations aid in posterior leaflet opening during systole.

On the atrial surface of the leaflets there exist two zones, the peripheral smooth zone and the central coaptation zone. The two areas are separated by the gently curved coaptation line between the two leaflets evident from atrial view.

Mitral valve 66 and tricuspid valve 60 regurgitation is present when the respective valves 66, 60 do not close completely, causing blood to leak back into the respective atria 56, 54.

Figure 2:
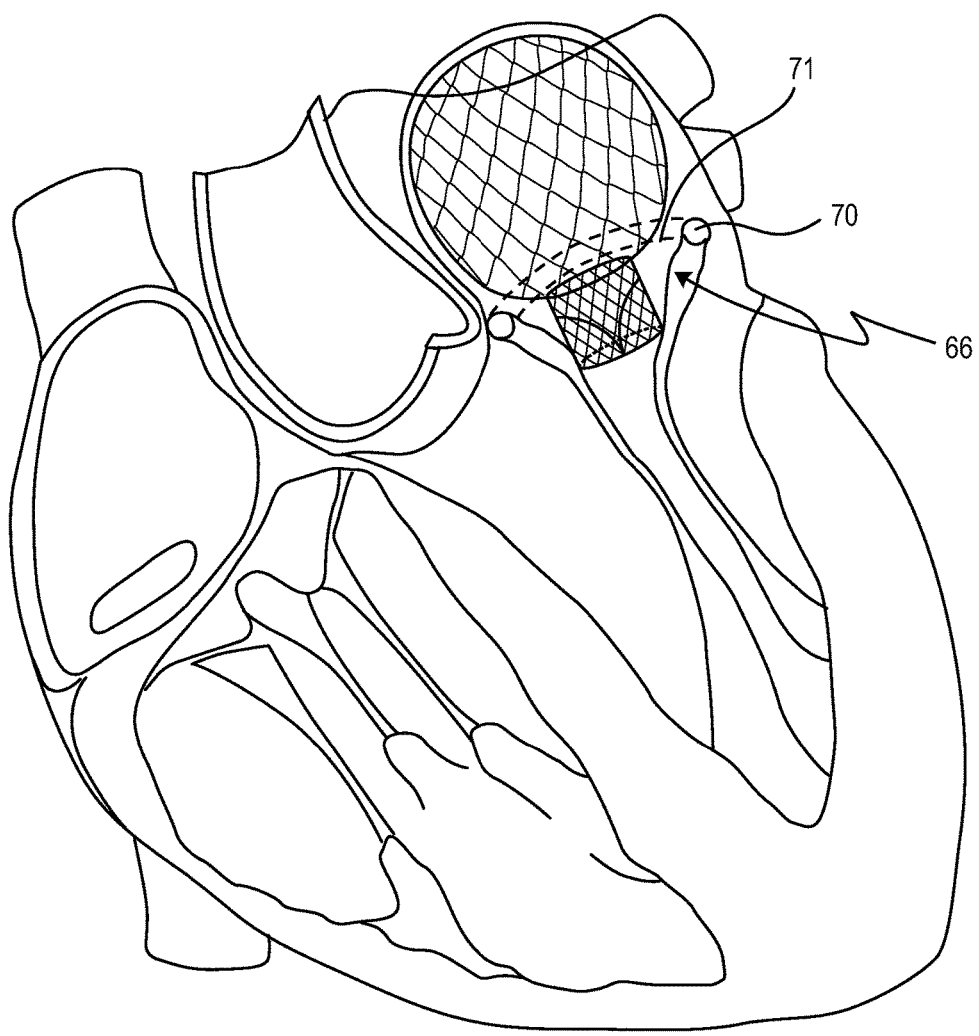
FIG. 2 shows a schematic drawing of an exemplary embodiment of the device placed in the correct position in the left atrium of a heart.

With the device according to the invention, heart valve regurgitation, in particular mitral valve regurgitation is to be treated, and placement of an exemplary embodiment of the device according to the invention is depicted in the attached FIG. 2.

FIG. 2 shows the schematic drawing of the heart as already depicted in FIG. 1. For better understanding, FIG. 2 does not include all of the reference numbers as depicted in FIG. 1, but is meant to show the same features of the human heart 50, with slight differences in the drawings.

As can be seen in FIG. 2, the device 10 according to the invention is placed in the expanded state in the human heart 50. The device as such is shown in more detail in FIG. 3A, and in the following it will be made reference to both, FIGS. 2 and 3A (to 3D); for the sake of better understanding, not all of the features of the device designated in FIG. 3 are designated in FIG. 2, however, the features are nevertheless the same.

Figure 3A:
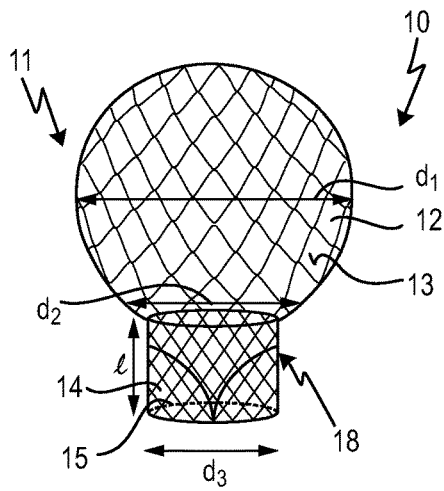
FIGS. 3A-3D are schematic drawings of various exemplary embodiments of the device displaying various designs.
Figure 3B:
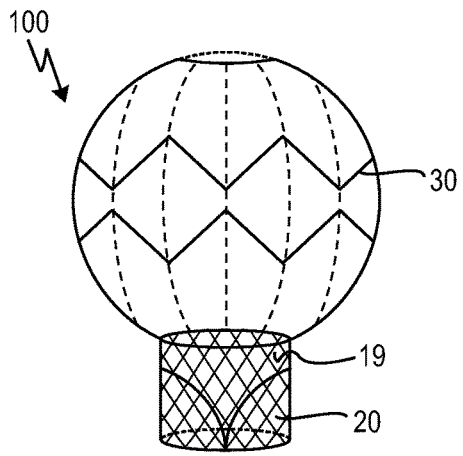
Figure 3C:
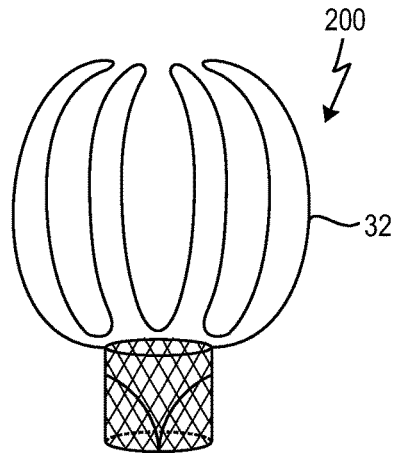
Figure 3D:
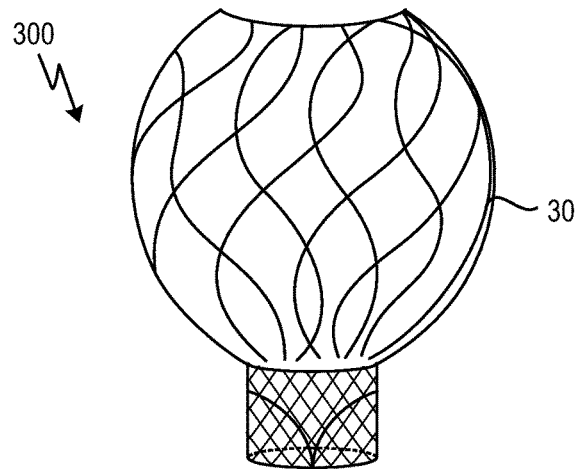

In FIG. 2, the exemplary implantable device 10 according to the invention—as shown in more detail in FIG. 3A and as it is possible with alternative shapes of the devices 100, 200, 300 shown in FIGS. 3B, 3C and 3D—is positioned in the left atrium 56 of the heart 50 in an expanded state of the device 10.

The implantable device 10 comprises a stent element 11 consisting of an atrial anchoring stent-portion 12 and an valve-carrying stent-portion 14, wherein the atrial anchoring stent-portion 12 and the valve-carrying stent-portion 14 are fixedly connected with one another, and are preferably integrally formed, i.e. manufactured as one piece.

In the expanded state of the device 10, the atrial anchoring stent-portion 12 of the stent-element 11 has a balloon-like shape 13, or, so to say, a spherical or ball-like shape, made of a stent-frame or stent-mesh 16, which is preferably laser-cut or interwoven or braided from a nitinol tube or nitinol wires.

With its outermost boundary 17, the atrial anchoring stent-portion 12, contacts the walls (not shown) of the left atrium 56, thus securely anchoring the device in the left atrium, without contacting the annulus 70 of the native valve 66. This is accomplished by the atrial anchoring stent-portion 12 of the stent-element 11 having, at its broadest or largest circumference, a diameter d1 which is larger than the diameter 71 of the annulus 70, and by the valve-carrying stent-portion 14 having a cylindrical shape 15 with a continuous diameter D3 along its cylindrical length l, which in turn is smaller than the diameter of the annulus 70 of the native heart valve 66, being mounted on the atrial anchoring stent-portion 12 such, that the atrial anchoring stent-portion does not contact or touch the annulus or reach into the intra-annular space.

Also, due to the valve-carrying stent-portion's 14 smaller diameter d3 it does not contact or touch the annulus 70 of the native valve 66, which is why the remaining yet dysfunctional closing-movement of the native valve 66 is retained.

As mentioned above, the valve-carrying stent-portion 14 has a cylindrical shape 15 with a continuous diameter d3. attached to the valve-carrying stent-portion 14 is a valve element 18. The valve-element 18 comprises a skirt-portion 19 and a valve-portion 20, the skirt-portion 19 being externally mounted to the valve-carrying portion 14, and the valve-portion 20 being internally mounted to the valve-carrying stent-portion 14. The valve-element 18 can be of any suitable material, preferably pericardium. The valve-portion 20 can be, e.g. a tri-, bi-, or monocuspid valve-portion 20, and can be derived, e.g. from a mammal.

It is to be understood that the valve portion 20 has the functions of a native valve, i.e. can open and close as a native valve does. As a consequence, upon implantation of the device 10, 100, 200, 300 of the invention, there are—so to speak—two valves opening and closing, i.e. the native valve and the valve 20 of the device 10, 100, 200, 300, instead of one native (mitral) valve 66. As a consequence, the valve-element 18 supports the closure of the native mitral valve's 66 closure.

According to the invention, the device 10 provides for a valve 20 with diameter d3 smaller than the native valve's annulus 70, which valve 20 will be positioned n an intra-annular position by means of the spherical self-expandable atrial anchoring stent-portion 12 placed inside the left atrium 56 and fixed in the atrium 56 by radial force of the stent-element 11. As the internal atrial main cavity has an almost spherical anatomy, the atrial anchoring stent-portion 12 of the device 10, 100, 200, 300 according to the invention, and using a ball-in-ball radial compression arrangement, provides for the necessary stability to keep the implanted valve device 10, 100, 200, 300 inside the intra annular space without contacting or touching the annular structure 70.

This hybrid solution, i.e. (mitral) valve replacement plus enhanced coaptation, also solves the drawback of the so-called spacer technique, i.e. thrombus formation and stenosis behaviour of the spacer.

The device 10, 100, 200, 300 can be implanted, e.g. via transcatheter means or surgically implanted. When using a catheter, the device 10, 100, 200, 300 according to the invention is loaded onto the catheter in a compressed state, which is retained by a tube or sheath (not shown) guided over the device 10, 100, 20, 300 thus compressing it. The catheter having loaded thereon the device 10, 100, 200, 300 according to the invention, may be introduced via the vessels of the patient and into the heart: For a mitral application, a direct apical access via the left ventricle apex and across the mitral valve to the left atrium is possible, but also a femoral vein or jugular vein access followed by trans-septal crossing to the left atrium and via pulmonic veins with small thoracotomy. For tricuspid application, a femoral vein or jugular vein access via the inferior or superior vena cava to the right atrium is possible. In the respective atrium—upon removal/withdrawing of the sheath—the expandable device 10, 100, 200, 300 is allowed to expand into its expanded state, thereby contacting and forcing itself against the atrial walls. As a consequence, the atrial anchoring stent-portion 12 of the device 10, 100, 200, 300 gets anchored within the atrium 56, while the valve-carrying stent-portion 14 is positioned intra-annular where its valve-element 18 supports the native valve 66.

FIGS. 3B, 3C and 3D show exemplary embodiments 100, 200, 300 of a device. Despite being manufactured differently, they all share the same shape, which is characterized by the balloon-like shape of the atrial anchoring stent-portion 12 and the cylindrical valve-carrying stent-portion 14 attached thereto.

FIG. 3B shows an embodiment, where the atrial anchoring stent-portion is made from stent rings circumferentially meandering in zigzag form, whereby the stent rings, in a longitudinal direction, are connected by additional (nitinol) wires, thus providing for a stent-frame.

FIG. 3C shows an embodiment where the balloon-like shape of the atrial anchoring stent-portion 12 is made from metal wires, preferably nitinol wires, with the wire(s) being outwardly, i.e. convex, finger-like bended or curved.

FIG. 3D shows an embodiment where the atrial anchoring stent-portion 12 is formed from metal wires interwoven or braided into a ball-like/spherical form.

The valve-carrying stent-portions 12 of the different embodiments shown in FIG. 3A to 3D are—substantially—manufactured in the same way, and represent a cylindrical tubular stent frame.

What is claimed is:

1. Implantable device for treating mitral valve regurgitation, the device being configured to expand from a compressed state into an expanded state, and comprising:
    a stent element comprising
    an atrial anchoring stent-portion, and
    a valve-carrying stent-portion,
    the atrial anchoring stent-portion being fixedly connected with the valve-carrying stent-portion,
    wherein the atrial anchoring portion, in the expanded state of the device, has a balloon-like shape and is so dimensioned as to have a diameter which is larger than a diameter of an annulus of a native mitral valve present between an atrium and a ventricle of a heart to be treated, and is so dimensioned and configured to anchor the device via radial force in an atrium of a heart to be treated when the device is in the expanded state,
    wherein the valve-carrying stent-portion, in the expanded state of the device, has a substantially cylindrical shape with a diameter (d3) which, in the expanded state, is so dimensioned as to be smaller than a diameter of an annulus of a native mitral valve of a heart to be treated, such that there is no contact between the annulus of the native mitral valve and the valve-carrying stent-portion; and
    a valve element comprising a skirt-portion and a valve-portion, the skirt-portion being externally mounted to the valve-carrying stent-portion, and the valve-portion being internally mounted to the valve-carrying stent-portion.

2. The device of claim 1, wherein, when implanted, the valve-element is so dimensioned and configured such that the native mitral valve's function is supported without replacing or impairing the native mitral valve's function.

3. The device of claim 1, wherein the atrial anchoring stent-portion and the valve-carrying stent-portion are integrally formed.

4. The device of claim 1, wherein the atrial anchoring stent-portion is configured to be anchorable in an atrium of a heart.

5. The device of claim 1, wherein the skirt-portion and the valve-portion of the valve element are made of a same material.

6. The device of claim 5, wherein the skirt-portion and the valve-portion of the valve element are made of pericardium.

7. The device of claim 1, wherein the valve element is a bi- or tri-leaflet valve.

8. The device of claim 1, wherein the stent-element is made of a shape-memory material.

9. The device of claim 8, wherein the stent-element is a laser-cut stent-element and/or composed of wires.

10. The device of claim 8, wherein the atrial anchoring stent-portion and/or the valve-carrying stent-portion is made from braided or otherwise intersected wires.

11. The device of claim 8, wherein the atrial anchoring stent-portion and/or the valve-carrying stent-portion is made from wire-loops.

12. The device of claim 8, wherein the stent-element is made of ninitol.

13. The device of claim 1, wherein the substantially cylindrical shape of the valve-carrying stent-portion, in the expanded state of the device, has a substantially continuous diameter (d3) along its cylindrical length (l).

14. Method for treating mitral valve regurgitation, the method comprising the step of deploying the device as claimed in claim 1 in a heart of a patient in need of being treated.

* * * * *